United States Patent
Le Roux et al.

(10) Patent No.: US 8,425,556 B2
(45) Date of Patent: Apr. 23, 2013

(54) EXTRA-DISCAL INTERVERTEBRAL STABILIZATION DEVICE

(75) Inventors: Stéphane Le Roux, Lyons (FR); Philippe Laurito, Le Val de France (FR)

(73) Assignee: Spineway, Bron (FR)

( * ) Notice: Subject to any disclaimer, the term of this patent is extended or adjusted under 35 U.S.C. 154(b) by 0 days.

(21) Appl. No.: 13/386,457

(22) PCT Filed: Jul. 29, 2010

(86) PCT No.: PCT/FR2010/051626
§ 371 (c)(1),
(2), (4) Date: Feb. 8, 2012

(87) PCT Pub. No.: WO2011/012829
PCT Pub. Date: Feb. 3, 2011

(65) Prior Publication Data
US 2012/0130430 A1    May 24, 2012

(30) Foreign Application Priority Data
Jul. 31, 2009   (FR) ...................................... 09 55374

(51) Int. Cl.
*A61B 17/70* (2006.01)
(52) U.S. Cl.
USPC ............ 606/246; 606/257; 606/264; 606/300
(58) Field of Classification Search .................. 606/246, 606/254–278, 300–321
See application file for complete search history.

(56) References Cited

U.S. PATENT DOCUMENTS

| | | | |
|---|---|---|---|
| 5,520,688 A | 5/1996 | Lin | |
| 7,927,356 B2* | 4/2011 | Lim | 606/257 |
| 2004/0111091 A1 | 6/2004 | Ogilvie et al. | |
| 2009/0093846 A1* | 4/2009 | Hestad | 606/255 |
| 2009/0163954 A1 | 6/2009 | Kwak | |
| 2009/0171395 A1 | 7/2009 | Jeon et al. | |

FOREIGN PATENT DOCUMENTS

| | | |
|---|---|---|
| FR | 2 672 202 A1 | 8/1992 |
| FR | 2 694 182 A1 | 2/1994 |
| WO | 2007124249 A1 | 11/2007 |

OTHER PUBLICATIONS

International Search Report for International Application No. PCT/FR2010/051626, dated Jan. 14, 2011.

* cited by examiner

*Primary Examiner* — Eduardo C Robert
*Assistant Examiner* — Christina Negrellirodriguez
(74) *Attorney, Agent, or Firm* — Heslin Rothenberg Farley & Mesiti P.C.

(57) ABSTRACT

An extra-discal device for intervertebral stabilization includes at least one rigid part connected to pedicle screws by an element. This rigid part comprises a cylindrical body, each end of which is firmly attached to the element which is flexible and deformable so as to be linked to a part of a corresponding pedicle screw with reduced play to obtain a limited range of multidirectional movement in the sagittal, horizontal and frontal planes, while limiting translational movement to the axis of the screw.

10 Claims, 3 Drawing Sheets

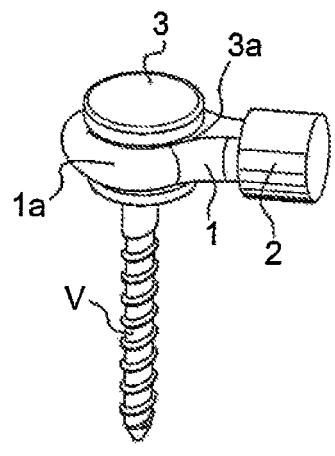
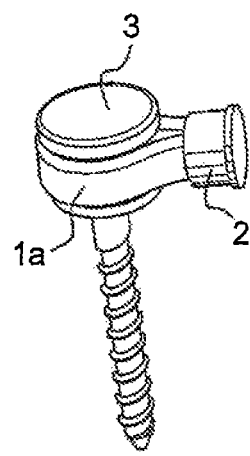
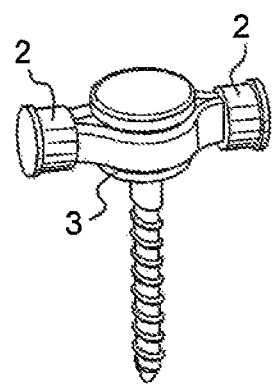
Fig. 8         Fig. 9         Fig. 10
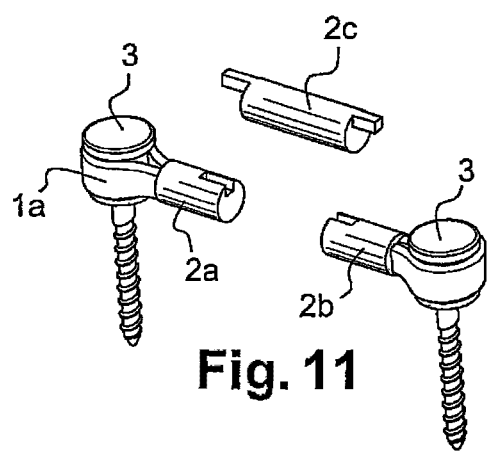
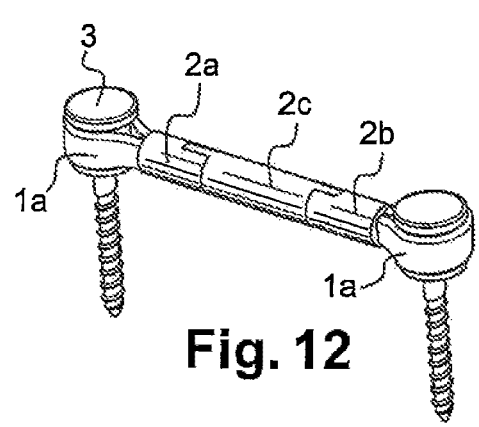
Fig. 11         Fig. 12
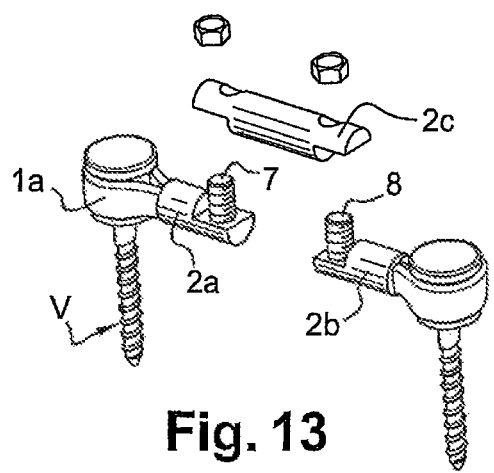
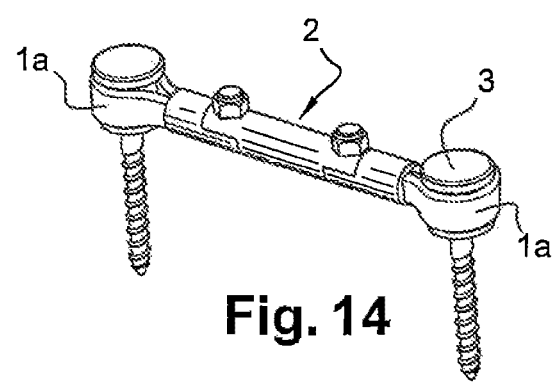
Fig. 13         Fig. 14

EXTRA-DISCAL INTERVERTEBRAL STABILIZATION DEVICE

CROSS REFERENCE TO RELATED APPLICATIONS

This application is a national stage filing under section 371 of International Application No. PCT/FR2010/051626, filed on Jul. 29, 2010, and published in French on Mar. 24, 2011, as WO 2011/012829 and claims priority of French application No. 0955374 filed on Jul. 31, 2009, the entire disclosure of these applications being hereby incorporated herein by reference.

BACKGROUND ART

The invention belongs to the technical sector of mechanisms for intervertebral stabilization.

The aim is to link at least two adjacent vertebrae in a manner known per se, to provide spinal stabilization allowing a range of movement between the vertebrae concerned.

Various technical solutions have been proposed to achieve this objective. For example, there is a system consisting of a ligament within a rigid tube arranged between two pedicle screws and attached to the said screws. This rigid tube is placed in compression between the two screws, consequently preventing any movement between the screws and the tube. The result is a rigid assembly generating stresses and strains on the implants with the risks of screws breaking or loosening.

Other systems with stems allow the vertebrae to be brought together, without however permitting any angulation movement between the said vertebrae which move while remaining parallel. The movement resulting from this is not therefore physiological.

According to the patent FR 2.672.202, a surgical implant is known that is composed of pedicle screws, the head of which has at least one radial shoulder defining at least one peripheral area for ligament retention. The link obtained is not sufficiently rigid and does not allow limitation of movement, particularly in extension. Because of this there is excessive demand on the facet joints and reduction in the intervertebral space through which the nerve roots pass. Excessive demand is also made on the disc.

Another solution can be found in patent FR 2.694.182 which describes an attachment for interpedicular prostheses, consisting of a fixation stem with a cylindrical support bearing at its end, a spherical head. A ligament, the ends of which are arranged into loops, connects the spherical heads of two consecutive stems. Before the ligament is fitted to the spherical heads, it may pass through a tightening ring. This solution is not satisfactory and requires complex fitting with the need for a ring to be mounted on the spherical head which is assembled so that it can move on the cylindrical support of the fixation stem. The ring is not adjusted relative to the spherical head. This results in a wide range of movement.

The objective of the invention is to remedy these disadvantages in a simple, safe, effective and rational manner.

The problem that the invention proposes to solve is obtaining stabilization in the context of therapeutic treatment of pathological conditions of the lumbar spine with the objective of conserving the height of the foramen and cohesion of the posterior articular facets and obtaining micromovements between the two instrumented vertebrae.

BRIEF SUMMARY OF INVENTION

To solve this problem, an extra-discal intervertebral stabilization device has been designed and developed consisting of at least two pedicle screws cooperating with at least two different vertebrae, the said screws being connected by a linkage system comprised of at least one rigid part attached at each end to the screws via an element.

According to the invention, the rigid part is formed of a cylindrical body, each end of which is firmly attached to the element which is flexible and deformable so as to be linked to part of the corresponding pedicle screw in such a way as to create reduced play, determined to obtain a limited range of multidirectional movement in the sagittal, horizontal and frontal planes, while limiting translational movement to the axis of the screw.

For the present application, reduced play is taken to mean restoring the physiological range of movements between the vertebrae.

The device may be combined with other (anterior, posterior, rigid or non-rigid) implant systems for arthrodesis or non-arthrodesis indications, or may form an implant system sufficient in its own right, or it may be combined with a rigid posterior system.

In the event of association with a rigid posterior system, the aim of the dynamic stabilization is to reduce the risk of degeneration of the disc adjacent to the levels operated.

The objective sought is that the vertebrae should be able to make micromovements so that the column is stabilized in the most anatomical position possible.

To advantage, the flexible and deformable element is a ligament.

In a particular embodiment, where the element is attached to a part of the pedicle screw, it is made into a loop.

Several forms of embodiment maybe envisaged from this basic design:

The loop part of the flexible element is positioned in a groove on the head of the corresponding pedicle screw;

The loop part of the flexible element is positioned in a groove on a head-piece which can be fixed onto the corresponding pedicle screw.

To solve the problem of reducing the play between the screw and the ligament, the rigid part is composed of a body with a cylindrical section which may be flat, flattened or otherwise shaped.

In a particular embodiment, the body is monobloc and hollow at its ends, the flexible element being inserted and fixed into the said ends in such a way that the loops protrude from them.

In another embodiment, the cylindrical body is made of several parts with coupling fittings.

For example, the cylindrical body may have three parts composed of two end-pieces joined to the loop piece of the flexible element, and an intermediate connecting unit. At each end of the intermediate connecting unit are coupling fittings which connect with the complementary fittings on each end-piece.

According to another characteristic, the body has a dynamic system allowing compression/distraction movements.

BRIEF DESCRIPTION OF THE DRAWING FIGURES

The invention is explained below in more detail using the accompanying figures of drawings in which:

In views in perspective, FIGS. 1, 2 and 3 show different forms of embodiment of pedicle screw heads, for connecting with the flexible element in the form of a ligament.

FIGS. 4 and 5 are views in perspective showing two examples of embodiments of the flexible element, combined with a rigid stem in the form of a cylindrical body.

In views in perspective, FIGS. 6 and 7 show another form of embodiment in which the connecting element is mounted with end-pieces that screw onto a threaded support made at the ends of the pedicle screws.

In partial views in perspective, FIGS. 8, 9 and 10 show different solutions for fixing the flexible element with a round or flattened cross-section to the head of the screw.

In views in perspective, FIGS. 11, 12, 13 and 14 show forms of embodiment in which the cylindrical body is made of three parts with detachable coupling fittings.

FIG. 15 shows a form of embodiment in which the body has a locking system with lock-nut.

In views in perspective, FIGS. 16, 17 and 18 show various possible types of assembly spanning one or more levels.

DETAILED DESCRIPTION

The intervertebral extra-discal stabilization device consists of at least two pedicle screws (V) cooperating with at least two different vertebrae. The screws (V) are linked by a linkage assembly composed of a flexible element (1), particularly in the form of a ligament, combined with a rigid part (2). The rigid part (2) is connected at each end to the heads of the screws (V) by the flexible element (1) forming a loop at each end (1a). The play between the screw head considered and the ligament (1) is so determined as to create reduced play suitable for allowing a limited range of movement in the sagittal, horizontal and frontal planes.

The movements permitted occur around the axis of the head of the pedicle screw (3). The ligament (1) avoids stresses being propagated in the screw and the rigid part (2). As a result of this there is better distribution of effort between the linking assembly and the vertebral bodies of the level operated. As concentration of stresses on the implants is avoided, the risks of breakage are reduced.

Various forms of embodiment can be envisaged stemming from this basic design.

The part or parts of the ligament (1) arranged in the form of a loop (1a), is/are placed in position around the screw head (3) of the pedicle screw being considered (V).

Different solutions may be envisaged for producing the screw head (3).

In FIG. 1, the screw head (3) comprises a cylindrical support (3a) with, at the bottom, a retaining flange (3b). The upper end of the cylindrical support (3a) has a thread (3c) for fitting a nut (4).

In FIG. 2, the cylindrical support (3a) for engaging the loop (1a) of the ligament (1) is formed directly during manufacture of the screw head (3), the said support (3a) having a circular groove. In this example of an embodiment, the ligament (1) has a flattened cross-section.

In FIG. 3, the circular groove (3a) is clearly concave. In this form of embodiment, the cross-section of the ligament (1) is round.

In another embodiment, in FIGS. 6 and 7, the heads (5) of the pedicle screws (V) are in the form of a screw thread suitable for screwing on end-pieces (6) which may be made in the same way as the screw heads (3) so as to provide a groove (6a) for positioning the ligament (1).

FIGS. 8 and 9 in particular show two examples of mounting and positioning the loop (1a) of a ligament with a round cross-section (FIG. 8) or a flattened cross-section (FIG. 9) relative to the screw head (3) or the end-piece (6), however these may have been made.

The loop (1a) of the ligament (1) may, for example, be crimped in the factory onto the end of the rigid part (2) in such a way as to obtain, between the screw (V) and the end of the rigid part (2) where the loop (1a) of the ligament (1) appears, reduced play (J) determined to permit a range of movement such that the micromovements allowed occur, as indicated, around the axis of the head of pedicle screw, in the sagittal direction and in the horizontal and frontal planes.

Without departing from the context of the invention, the link between the ligament (1) and the screw head (3) may be made by arrangements other than a loop.

The rigid part (2) is made, for example, in the form of a cylindrical body, according to various designs. For example, as figure 4 shows, the cylindrical body (2) is monobloc and hollow at each of its ends, the ligament (1) being inserted and fixed in the said ends in such a way that the loops (1a) protrude.

In FIGS. 11 to 14, the cylindrical body (2) comprises several parts with coupling mechanisms. For example, the body (2) is produced in three parts composed of two end-pieces (2a) and (2b) joined by any appropriate means to the loop part (1a) of the ligament (1). The ends of the two end-pieces (2a) and (2b) have coupling mechanisms which interact with the complementary coupling mechanisms of an intermediate part (2c). These complementary coupling mechanisms may be composed, for example, of mortise and tenon arrangements (FIGS. 11 and 12) or they may be in the form of pins (7)-(8) on the end-pieces, (2a) and (2b), which engage in holes in the intermediate part (2c) to work with assembly devices.

In an embodiment illustrated in FIG. 15, the body (2) has a locking system (9) with lock-nuts allowing compression/distraction movements. The body (2) may be fitted with a dynamic system.

Finally, FIGS. 16, 17 and 18 show various types of assembly of the dynamic stabilization device according to the invention.

Figure 1:
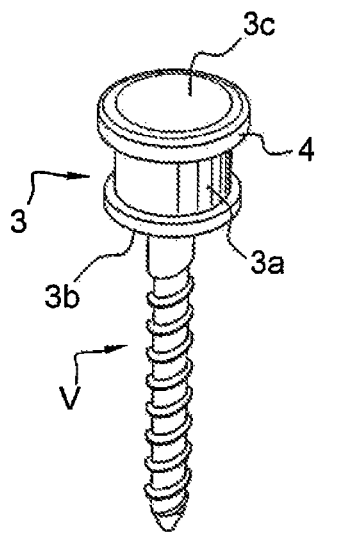
Figure 2:
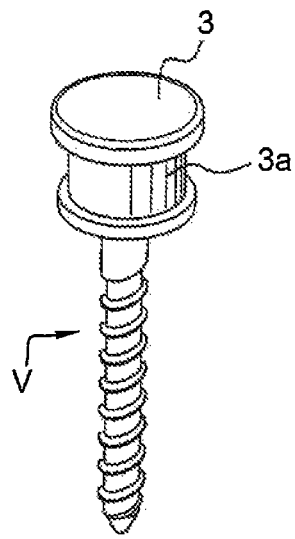
Figure 3:
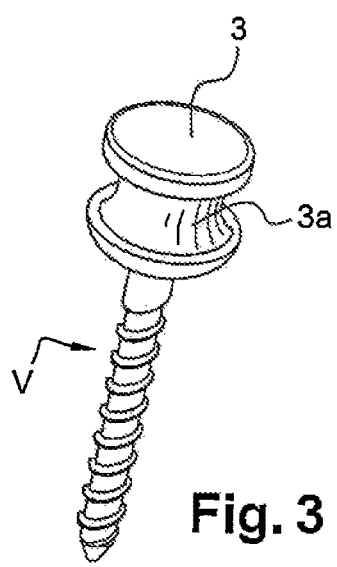
Figure 4:
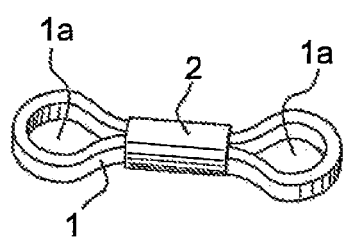
Figure 5:
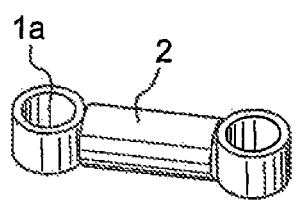
Figure 6:
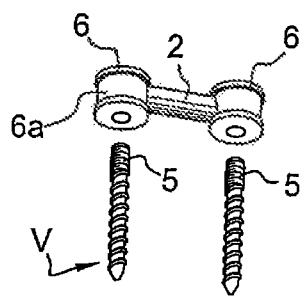
Figure 7:
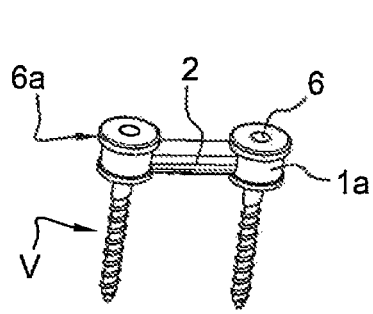
Figure 15:
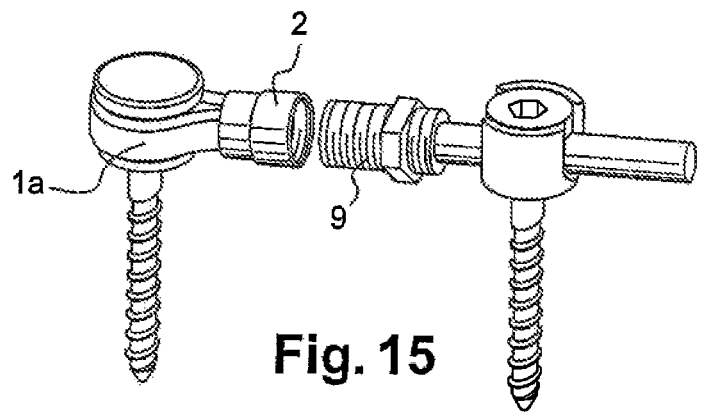
Figure 17:
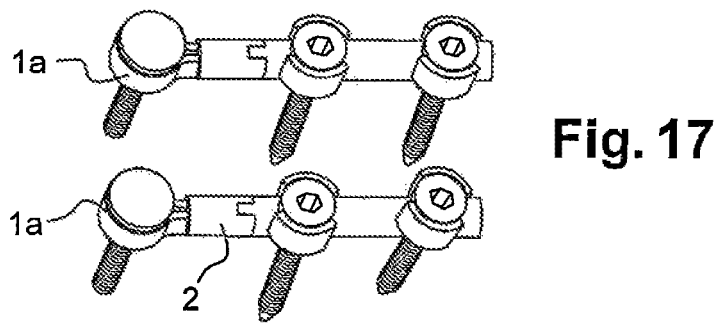
FIG. 17 shows a rigid assembly on one level with a flexible assembly on another.
Figure 18:
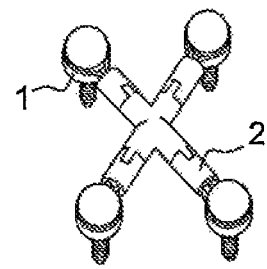
FIG. 18 shows a cruciform assembly.
Figure 16:
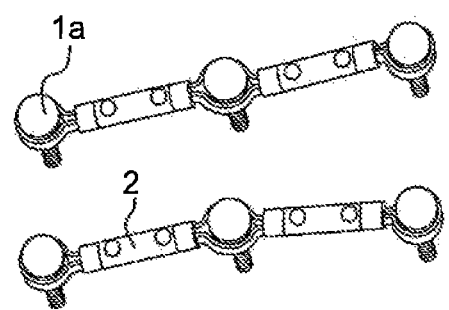
FIG. 16 shows a rigid assembly spanning two levels.

The advantages are clearly obvious from the description.

The invention claimed is:

1. Extra-discal device for intervertebral stabilization including at least two pedicle screws cooperating with at least two different vertebrae, the screws being linked by a linkage assembly including at least one rigid part coupled to at least one pedicle screw by a loop of an element extending from inside a hollow end of the rigid part, wherein the rigid part comprises a cylindrical body, the element being fixed inside a hollow end of the cylindrical body, and the element being flexible and deformable and linked by the loop to a part of the at least one pedicle screw with reduced play to obtain a limited range of multidirectional movements in sagittal, horizontal and frontal planes while limiting translational movement to an axis of the at least one pedicle screw.

2. Device according to claim 1, wherein the flexible and deformable element is a ligament.

3. Device according to claim 1, wherein the loop attaches to a head part of the at least one pedicle screw.

4. Device according to claim 3, wherein the loop is positioned in a groove on a head of the at least one pedicle screw.

5. Device according to claim 3, wherein the loop is positioned in a groove on a head-piece fixed onto the at least one pedicle screw.

6. Device according to claim 1, wherein the cylindrical body comprises a single part hollow at both ends, the element being inserted and fixed inside each hollow end of the body in such a way that a loop protrudes from each hollow end.

7. Device according to claim 1, wherein the cylindrical body comprises several parts with coupling arrangements.

8. Device according to claim 7, wherein the cylindrical body comprises two end-pieces each joined to a loop of the element inside a hollow end of a respective end-piece, and an intermediate linking part.

9. Device according to claim 8, wherein the intermediate linking part has coupling arrangements at each end cooperating with coupling arrangements on each end-piece.

10. Device according to claim 1, wherein the cylindrical body has a system allowing compression/extension movements.

* * * * *